US00PP23519P2

(12) United States Plant Patent
Smith

(10) Patent No.: US PP23,519 P2
(45) Date of Patent: Apr. 9, 2013

(54) ***CHRYSANTHEMUM* PLANT NAMED 'SYHES HORED'**

(50) Latin Name: *Chrysanthemum×morifolium*
Varietal Denomination: Syhes Hored

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 249 days.

(21) Appl. No.: 13/065,871

(22) Filed: Mar. 31, 2011

(51) Int. Cl.
*A01H 5/00* (2006.01)

(52) U.S. Cl. ..... Plt./287

(58) Field of Classification Search ..... Plt./287, Plt./290, 293
See application file for complete search history.

*Primary Examiner* — Kent L Bell
(74) *Attorney, Agent, or Firm* — Joshua L. Price

(57) ABSTRACT

A new *Chrysanthemum* plant named 'Sykes Hored' particularly distinguished by the long-lasting orange-red inflorescence color, medium green foliage, good mounding plant habit, and a natural flowering season response that is about mid September.

1 Drawing Sheet

Latin name of the genus and species of the plant claimed: *Chrysanthemum×morifolium.*

Varietal denomination: 'Syhes Hored'.

BACKGROUND OF THE NEW PLANT

The present invention comprises a new *Chrysanthemum*, botanically known as *Chrysanthemum×morifolium*, and hereinafter referred to by the variety name 'Syhes Hored'.

'Syhes Hored' is a product of a planned breeding program. The new cultivar has long-lasting orange-red inflorescence color, medium green foliage, good mounding plant habit, and a natural flowering season response that is about mid September.

'Syhes Hored' originated from a hybridization made in December 2006 in a controlled breeding environment in Tenjo, Colombia. The female parent was the proprietary plant designated 'Yobrandi', U.S. Plant Pat. No. 16,134, with lighter red inflorescence color, more width to the plant habit and 7-10 days slower flowering response in the fall in the north.

The male parent of 'Syhes Hored' identified as 'Cyclops', an unpatented variety, with smaller, lighter red inflorescences, more disk florets, less mounding and a bit more upright plant habit and a natural flowering season response that is 5-7 days slower. The resultant seed was sown in June 2007 in Alva, Fla. USA.

'Syhes Hored' was selected as one flowering plant within the progeny of the stated cross in the November 2007 in a controlled environment in Alva, Fla.

The first act of asexual reproduction of 'Syhes Hored' was accomplished when vegetative cuttings were propagated from the initial selection in December 2007 in a controlled environment in Alva, Fla.

BRIEF SUMMARY OF INVENTION

Horticultural examination of plants grown from cuttings of the plant initiated in December 2007, and continuing thereafter, has demonstrated that the combination of characteristics as herein disclosed for 'Syhes Hored' are firmly fixed and are retained through successive generations of asexual reproduction.

'Syhes Hored' has not been observed under all possible environmental conditions. The phenotype may vary significantly with variations in environment such as temperature, light intensity and day length.

A Plant Breeder's Right for this cultivar was applied for in Canada on Apr. 9, 2010 (No. 10-6931). 'Syhes Hored' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Syhes Hored' with colors being as true as possible with an illustration of this type. The photographic drawing shows a flowering potted plant of the new variety.

DETAILED BOTANICAL DESCRIPTION

The plant used for the photographs was about 12 weeks old, grown in Monroeville, N.J., in an outdoor trial. Rooted cuttings were grown in a nine inch pot with no terminal pinching of the apices. The photograph was taken in mid-September 2010 in New Jersey.

The plant descriptions and measurements were taken in Gilroy, Calif. in May 2010 under natural light. Plants were grown under conditions which approximate those generally used for potted chrysanthemum trials in a greenhouse. These plants used in the descriptions were about 10 weeks old.

Color references are made to The Royal Horticultural Society Colour Chart (R.H.S.) 2001.

TABLE 1

DIFFERENCES BETWEEN THE NEW VARIETY 'SYHES HORED' AND A SIMILAR VARIETY

| | 'Syhes Hored' | 'Helen' (U.S. Plant Pat. No. 9,793) |
|---|---|---|
| Ray floret color: | RHS N34A | RHS 46A to RHS 185A |
| Disc floret color: | RHS 155A base with RHS 3A apex | RHS 14B |
| Foliage color: | Closest to RHS 137A | RHS 147A |
| Plant habit: | Rounder/wider | More upright/less width |
| Peduncle length: | Stronger | Weaker |

Plant:

*Form, growth and habit.*—Herbaceous decorative garden-type, stems upright and outwardly spreading, freely branching, strong and moderately vigorous growth habit.

*Plant height.*—12-14 cm.

*Plant height* (*inflorescence included*).—17-19 cm.

*Plant width.*—25 cm.

*Garden performance and tolerance to weather.*—Very good.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137A.

*Lower surface.*—Closest to RHS 137B.

*Mature, leaf color, upper surface.*—Closest to RHS 137A.

*Lower surface.*—Closest to RHS 137B.

*Length.*—5.0-5.5 cm.

*Width.*—3.3-3.7 cm.

*Shape.*—Ovate.

*Base shape.*—Attenuate.

*Apex shape.*—Mucronulate.

*Margin.*—Irregularly and palmately lobed; serrate.

*Texture, upper surface.*—Bifid T-shaped hairs.

*Lower surface.*—Bifid T-shaped hairs.

*Color of veins, upper surface.*—RHS 144B.

*Color of veins, lower surface.*—RHS 144B.

*Petiole color.*—RHS 144B.

*Length.*—1.0 cm.

*Diameter.*—0.3 cm.

*Texture.*—Bifid T-shaped hairs.

Stem:

*Quantity of main branches per plant.*—3-4.

*Color of stem.*—RHS 146B.

*Length of stem.*—13-15 cm.

*Diameter.*—0.3-0.4 cm.

*Length of internodes.*—0.5-1.5 cm.

*Texture.*—Bifid T-shaped hairs.

*Color of peduncle.*—RHS 146B but appears lighter because of hairs.

*Length of peduncle.*—5.0-6.0 cm.

*Peduncle diameter.*—0.15 cm.

*Texture.*—Bifid T-shaped hairs.

Inflorescence:

*Type.*—Compositae type, solitary inflorescences decorative-type, borne terminally above foliage, ray florets arranged acropetally on a capitulum.

*Quantity of short days to flowering* (*response time*).—About 48 days.

*Quantity of inflorescences per plant.*—Approximately 75, plus many buds.

*Lastingness of individual blooms on the plant.*—More than 6 weeks from the first color.

*Fragrance.*—Slightly spicy.

Bud (just when opening/showing color):

*Color.*—RHS 178B.

*Length.*—0.9-1.2 cm.

*Width.*—1.0 cm.

*Shape.*—Oblate.

Immature inflorescence:

*Diameter.*—3.0-3.8 cm.

*Color of ray florets, upper surface.*—A slight base of RHS 3C heavily overlaid with RHS N34A but velvety looking.

*Lower surface.*—RHS 3C base overlaid RHS 172A.

Mature inflorescence:

*Diameter.*—4.5 cm.

*Depth.*—1.5-1.8 cm.

*Total diameter of 'disc'.*—0.5-0.6 cm.

*Receptacle height.*—0.3 cm.

*Receptacle diameter.*—0.4-0.5 cm.

Ray florets:

*Average quantity of florets.*—About 90 in numerous whorls.

*Color of florets, upper surface.*—A slight base of RHS 3C heavily overlaid with a slightly muted shade of RHS N34A but still velvety looking.

*Lower surface.*—RHS 3C base overlaid RHS 172C with RHS 172B margins.

*Length.*—2.2-2.5 cm.

*Width.*—0.6 cm.

*Shape.*—Obovate.

*Apex shape.*—Praemorse.

*Margin.*—Entire.

*Texture, upper surface.*—Papillose.

*Lower surface.*—Papillose.

Disc florets:

*Average quantity of florets.*—Approximately 20.

*Color of florets.*—RHS 155A base with RHS 3A apex.

*Length.*—0.5 cm.

*Width.*—0.1 cm.

*Shape.*—Tubular, elongated.

*Apex shape.*—Acute, 5 pointed.

Phyllaries:

*Quantity.*—20-25.

*Color, upper surface.*—RHS 138A.

*Lower surface.*—RHS 138A but appears lighter with hairs.

*Length.*—0.6-0.7 cm.

*Width.*—0.3-0.4 cm.

*Shape.*—Ovate.

*Apex shape.*—Acute.

*Base.*—Fused.

*Margins.*—Entire; Papery.

*Texture, upper surface.*—Bifid T-shaped hairs.

*Lower surface.*—Bifid T-shaped hairs.

Reproductive organs:

*Pistil.*—1.

*Length.*—0.5 cm.

*Style color.*—RHS 1C.

*Style length.*—0.4 cm.

*Stigma color.*—RHS 3A.

*Stigma shape.*—Bi-parted.

*Ovary color.*—Not observed.

*Stamens.*—1.

*Color of filaments.*—RHS 1C.

*Length filaments.*—0.3-0.4 cm.

*Anther color.*—RHS 2B.

*Anther length.*—0.1 cm.

*Anther shape.*—Oval.

*Color of pollen.*—Not observed.

*Pollen amount.*—Not observed.

*Fertility/seed set.*—Has not been observed on this hybrid.

Disease/pest resistance: Disease/pest resistance has not been observed on this hybrid.

What is claimed is:

1. A new and distinct variety of *Chrysanthemum* plant named 'Syhes Hored' substantially as illustrated and described herein.

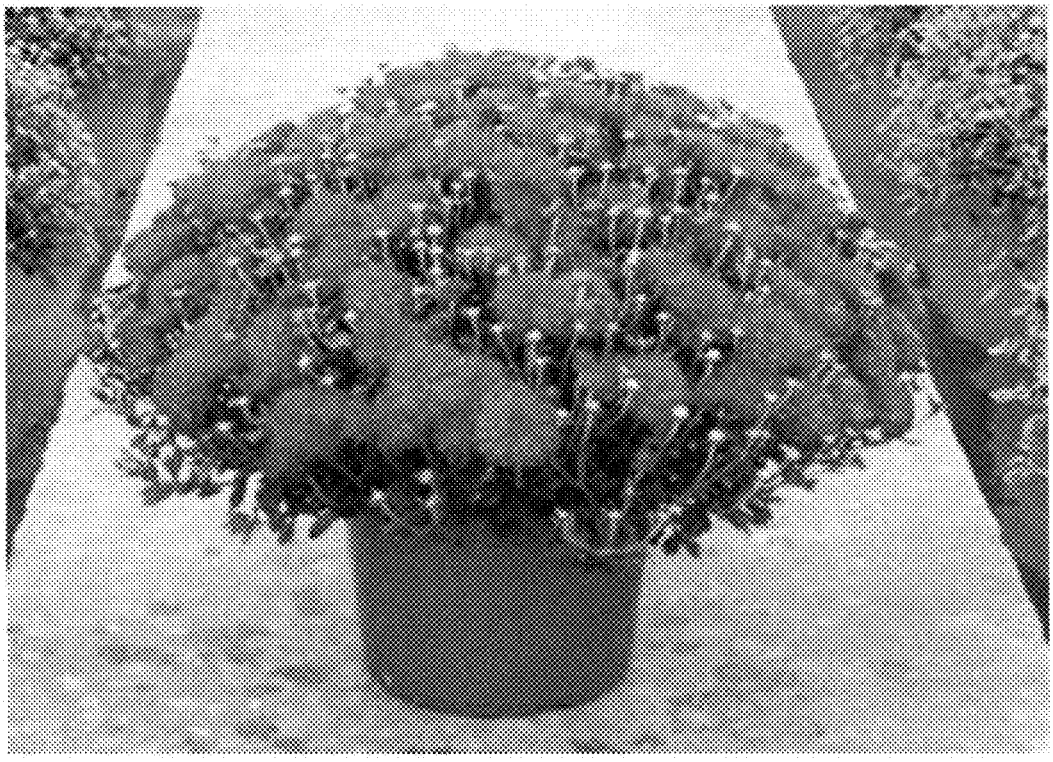

* * * * *